United States Patent [19]
Salvador et al.

[11] Patent Number: 5,315,367
[45] Date of Patent: May 24, 1994

[54] METHOD TO DETECT MAN-MADE FIBERS AND/OR DEFECTIVE FIBERS AND/OR OTHER FOREIGN MATERIALS IN THE PROCESSING OF SILK WASTE, AND RELATIVE APPARATUS

[75] Inventors: Pierantonio Salvador, Udine; Paolo Viciguerra, Rivignano, both of Italy

[73] Assignee: Cascami Seta-Filature Seriche Riunite SpA, Vallemosso, Italy

[21] Appl. No.: 981,397

[22] Filed: Nov. 25, 1992

[30] Foreign Application Priority Data

Nov. 29, 1991 [IT] Italy .................. 91A000201

[51] Int. Cl.$^5$ ............................. G01N 21/00
[52] U.S. Cl. .................... 356/238; 356/239; 356/430; 356/73
[58] Field of Search ............... 356/237, 239, 238, 429, 356/430, 431, 73, 73.1, 390, 394, 398; 250/559-563, 571, 572, , 225; 19/3, 80 R, 81

[56] References Cited

U.S. PATENT DOCUMENTS

| | | |
|---|---|---|
| 2,824,488 | 2/1958 | Bridges . |
| 3,421,820 | 1/1969 | Heubschman ............ 356/238 |
| 3,841,761 | 10/1974 | Selgin ...................... 356/430 |
| 4,692,799 | 9/1987 | Saitoh et al. ............. 350/562 |
| 4,839,943 | 6/1989 | Leifeld .................... 19/80 |
| 4,865,445 | 9/1989 | Kuriyama et al. ....... 356/73 |
| 5,068,799 | 11/1991 | Jarrett, Jr. .............. 356/238 |

FOREIGN PATENT DOCUMENTS

| | | |
|---|---|---|
| 0412447 | 8/1990 | European Pat. Off. . |
| WO91/11705 | 8/1991 | PCT Int'l Appl. . |
| 808505 | 9/1955 | United Kingdom . |
| 2242266 | 9/1991 | United Kingdom . |

Primary Examiner—Richard A. Rosenberger
Assistant Examiner—Hoa Q. Pham
Attorney, Agent, or Firm—Antonelli, Terry, Stout & Kraus

[57] ABSTRACT

Method to detect manmade fibres, defective fibres and/or other foreign materials in the processing of silk waste and to classify and count the faults detected in the lap of silk fibres leaving a drawing frame for instance, the method arranging that a substantially defined zone of the lap of silk fibres (20) made substantially parallel is illuminated by transparency with white light (23) and is scanned by a telecamera (24) associated with a data processing system (27) and is also illuminated by transparency with polarized light (25) and is scanned at the same time by a telecamera (26), which too is associated with the data processing system (27), images (14–15) taken by the telecameras (24–26) being processed and compared to determine the quantity, position, type and length of the faults of manmade, foreign or defective fibres. Apparatus to detect manmade fibres in the processing of silk waste in the form of fibres and to classify and count faults detected in a lap of silk fibres leaving a drawing frame, for instance, the apparatus comprising a transparent surface (36) on which is laid a lap of silk fibres (20) made substantially parallel, on which are present a first source of light and a second source of light, one of the sources being a source of white light (23) while the other source is a source of polarized light (25), the sources of light cooperating with at least one telecamera (24–26) positioned on the opposite side of the transparent surface (36) and associated with a data processing unit (27) and an identification unit (13).

18 Claims, 1 Drawing Sheet

METHOD TO DETECT MAN-MADE FIBERS AND/OR DEFECTIVE FIBERS AND/OR OTHER FOREIGN MATERIALS IN THE PROCESSING OF SILK WASTE, AND RELATIVE APPARATUS

BACKGROUND OF THE INVENTION

This invention concerns a method to detect man-made fibers and/or defective fibers and/or other foreign materials in the processing of silk waste, and the relative apparatus.

To be more exact, the invention concerns a method and the relative apparatus to identify man-made fibers, advantageously but not only polypropylene fibers, defective fibers and/or other foreign materials included in laps of silk fibers coming from the processing of silk waste.

Moreover, the method and the relative apparatus according to the invention enable the faults detected in the lap of silk fibers to be classified and counted and to be sorted by types.

This method and the relative apparatus are applied advantageously to the textile industry, for instance downstream of a drawing frame, and in particular to the quality control step, whether that step is performed by sampling or not.

This control of quality can be carried out either by a classification of the laps of silk fibers on the basis of the man-made fibers and/or the defective fibers and/or other foreign materials encountered or by combining the control with successive apparatuses so as to eliminate such faults and/or such man-made or defective fibers thus identified.

It is known that during recent years the old packages based on cellulose in which silk wastes were conveyed from their collection points to their recovery and re-use points have been replaced by packages containing man-made fibers particularly polypropylene fibers.

The technology of the state of the art had already obtained a system to identify cellulose fibers in laps of silk fibers.

The technology of the state of the art has made possible the identification, on a lap of silk fibers leaving a drawing frame or like machine, of some types of faults by using the field of the data processing of images.

The present technique of the data processing of images is carried out substantially in three different successive steps, and in particular by the acquiring of the image, the data processing of the image and the actual identification of a determined type of foreign or defective fibers or materials.

According to the known methods the lap of silk fibers is fed forwards at a set speed and is scanned by a telecamera connected to a computer into which is loaded a program that converts the visual image into data compatible for analysis.

Special algorithms make possible the identification of a series of faults present in the image taken by the telecamera, and the classification of the lap of silk fibers takes place on the basis of the faults detected.

But the technology of the state of the art is powerless in the case of man-made fibers and, in particular, polypropylene fibers. This situation therefore entails the shortcoming that these polypropylene fibers contaminate the silk fibers and impair the quality.

With the state of the art the various laps of silk fibers are classified automatically on the basis of the quantity and type of the faults.

This classification does not include the contamination by man-made fibers present in the lap of silk fibers since these man-made fibers are sometimes identified as being "not silk" but are not identified as being man-made fibers.

Such an improvement of the classification is still impossible as no method and therefore no apparatus exist for the identification of the man-made fibers present in laps of silk fibers.

At the present time the samples of laps of silk fibers are inspected visually by the appointed personnel, who try to detect any man-made fibers and, in particular, polypropylene in the lap of silk.

As this operation requires great care and concentration on the part of the machine operator, the present speed of inspection is about 0.4 to 0.5 meters of the lap of silk fibers per minute, and the outcome of this situation is that the classification of the laps of silk fibers is made on the basis of an inspection carried out on very small samples and that therefore the statistical results are sometimes not very reliable.

U.S. patent Application 4,839,943 discloses a device to detect faults such as natural or man-made foreign fibers, knotted strings, bunches of synthetic materials, pieces of thread within or between tufts of particular loose textile fibers such as cotton, wool, etc.

The foreign fibers are detected on the basis of their various characteristics, such as configuration and/or color and/or size and/or luminosity, but this method does not enable the faults to be detected by their type and limits itself only to the identification of everything which does not correspond to the fiber being processed at the time.

The device to detect faults comprises advantageously a means to transmit electromagnetic waves to a means which receives those waves, the two means being arranged opposite to each other on one side and the other side of the layer of fibers to be analysed.

The device to detect faults is of a camera or telecamera type and the images thus produced are stored and compared, by means of a suitable evaluation contrivance, with photographs stored in the device so as to identify as faults everything not consisting of the particular required fiber.

The detector device actuates a suitable removal means positioned downstream to remove the faults previously identified.

Furthermore, this device cannot count nor classify the various faults as being what they are but makes a rough evaluation of the fibers and identifies everything which is considered as material foreign to the actual fiber being examined.

The device is applied, in fact, to fibers which are not scoured nor beaten but are merely opened and spread on a conveyor belt; the fibers contain great quantities of impurities such as seeds, vegetable fragments, dusts, etc., and these impurities are included even in quantities consisting of some percentage by weight of the mass being processed.

WO-91/11705 discloses a method to measure optically the characteristics of quality and quantity of textile fibers. The method enables, in particular, the length, fineness, degree of maturity and curliness of the fibers, whichever they are, to be established at the same time.

The method is applied to a single-layer sample of fibers consisting of a limited number of fibers made parallel and positioned between two glasses but cannot be applied to laps of continuous fibers for an in-line analysis and inspection process. Moreover, this method does not lead to identification of faults in the sample of fibers analysed and therefore does not enable the sample under examination to be classified on the basis of the type and number of faults identified.

SUMMARY OF THE INVENTION

So as to overcome the shortcomings of the state of the art and to achieve further advantages the present applicants have studied, tested and obtained this invention.

The purpose of the invention is to identify automatically and reliably any man-made fibers and advantageously, but not only, polypropylene fibers and/or defective fibers and/or other foreign materials mixed with the discontinuous silk fibers in samples of laps of silk fibers coming from silk waste.

The method according to the invention makes possible also the detection of other types of faults such as hairs, knots, various contaminating fibers, defective fibers, etc.,the classification of faults according to their type and the counting of faults by classes of types.

The method for detection of the man-made fibers according to the invention is based on the known method of data processing of images and is carried out in the three known different steps of acquiring the image, processing the image and actually identifying the faults.

This method is applied to the lap of silk fibers leaving a drawing frame or a machine or equipment suitable to make the fibers extremely parallel.

According to the invention two telecameras are employed at the same time in the image acquiring step and scan the lap of silk fibers having its fibers substantially parallel; the two telecameras are characterized in that one of them uses a source of white light, whereas the other uses a source of polarized light.

According to the invention the lap of silk fibers is illuminated by transparency by the two sources of light.

A great part of the faults in the lap of silk fibers is detected by the telecamera with the source of white light.

All the faults connected with the inclusion of polypropylene fibers are detected by the telecamera with the source of polarized light.

In fact, the fibers foreign to the silk and therefore also the manmade fibers, including polypropylene fibers, are generally more opaque and therefore, as we said above, are detected by the telecamera with the source of white light.

The telecamera with the source of white light enables the characteristics parameters of the contaminating fibers to be identified such as thickness, length, lack of continuity and opacity, which are used thereafter to identify the type of contaminating fibers detected.

But as the polypropylene fibers along rotate the vector of polarization of the polarized light, the telecamera with the source of polarized light identifies only the polypropylene fibers.

Since the polypropylene fibers may have been "contaminated" by the treatment undergone by the silk or may be partly hidden by other fibers, the polarized light identifies the polypropylene fibers only partly but not their full extent.

According to a variant the source of white light is suitably filtered and/or colored.

According to another variant there is only one telecamera, which carries out its scanning operations in succession by illuminating the zone to be observed now with white light and then with polarized light.

According to the above variant the step of acquiring the images is performed in a discontinuous manner and the lap of silk fibers is fed forwards step by step.

The data processing step consists generally of three procedures, namely an accentuation procedure, a procedure of conversion into binary signals and a compression procedure.

The procedures of conversion into binary signals and of compression are of a known type and may possibly be cancelled in the method according to the invention.

In the method according to the invention the accentuation procedure has been modified so as to be able to accentuate the presence of contaminating fibers and of polypropylene fibers in particular.

During the step of accentuating the image scanned with white light all the fibers having a greater opacity are accentuated, thus identifying not only the slightly intertwined clusters of silk fibers but also all the contaminating fibers contained in the lap of silk fibers thus observed.

During the step of accentuating the image scanned with polarized light all the parts of the fibers are accentuated which rotate the plane of the polarized light, this being a typical feature of polypropylene fibers alone, as we said above.

In the third and last step of identification an analysis of the photograph taken by the telecamera with white light is carried out to identify the type of fault, while a combined analysis of the data obtained by data processing of the two separate image taken by the specific telecameras is carried out to identify the polypropylene fibers.

In fact, the analysis of the image taken with white light provides some characteristic parameters such as thickness, length, lack of continuity and opacity of the contaminating fibers.

For identification of the polypropylene fibers, instead, the image taken with the telecamera with polarized light provides the number and position of the polypropylene fibers, whereas the image taken with the telecamera with white light gives the extent of all the contaminating fibers.

By combining these data it is possible to obtain automatically the number of polypropylene fibers included and their respective lengths, thus providing information about the quality of the lap of silk fibers being examined.

In particular, the identification step includes substantially three successive steps, namely a first step to detect the characteristic parameters of the contaminating fibers, a second step to compare and catalogue the contaminating fiber and a third and last step to count the faults by types.

In particular, in the first step of detecting the characteristic parameters of the contaminating fibre the analysis of the image of the contaminating fibre taken with white light can provide parameters such as thickness, length, lack of continuity and opacity of the contaminating fiber.

In the second comparison and cataloguing step the above parameters are compared with an assembly of analogous values, each of which corresponds to a given class of faults, so as to catalogue the contaminating fiber in an exact class of faults.

The classes of faults are determined on the basis of fields of values of these characteristic parameters in such a way that the classes are separated nd detached from each other, thus enabling the contaminating fiber to be apportioned to one single class.

Where the values of the characteristic parameters are such that the foreign fiber cannot be listed in any of the classes identified above, the foreign fiber is catalogued as an "unidentified fault" and is apportioned to the corresponding class.

Upon the apportioning of a contaminating fibre to a particular class of fault a counter relating to the identified class of fault is set to a higher value.

In the third step the detected faults separated by types of fault and indicated by the counters relating to the various classes are taken into account.

With the apparatus according to the invention it is possible to inspect laps of silk fibers running at a speed of 3 to 10 meters per minute, advantageously 4 to 6 meters per minute, thus enabling greater samplings to be carried out on the lap of silk fibers in question and therefore providing more reliable statistical results.

According to a variant a mapping step is included after the identification step and can be employed in a machine or equipment so as to eliminate, even selectively, faults or parts of the same.

BRIEF DESCRIPTION OF THE DRAWINGS

The attached figures, which are given as a non-restrictive example, show a preferred solution of the invention as follows.

DETAILED DESCRIPTION OF THE PREFERRED EMBODIMENTS

Figure 1:
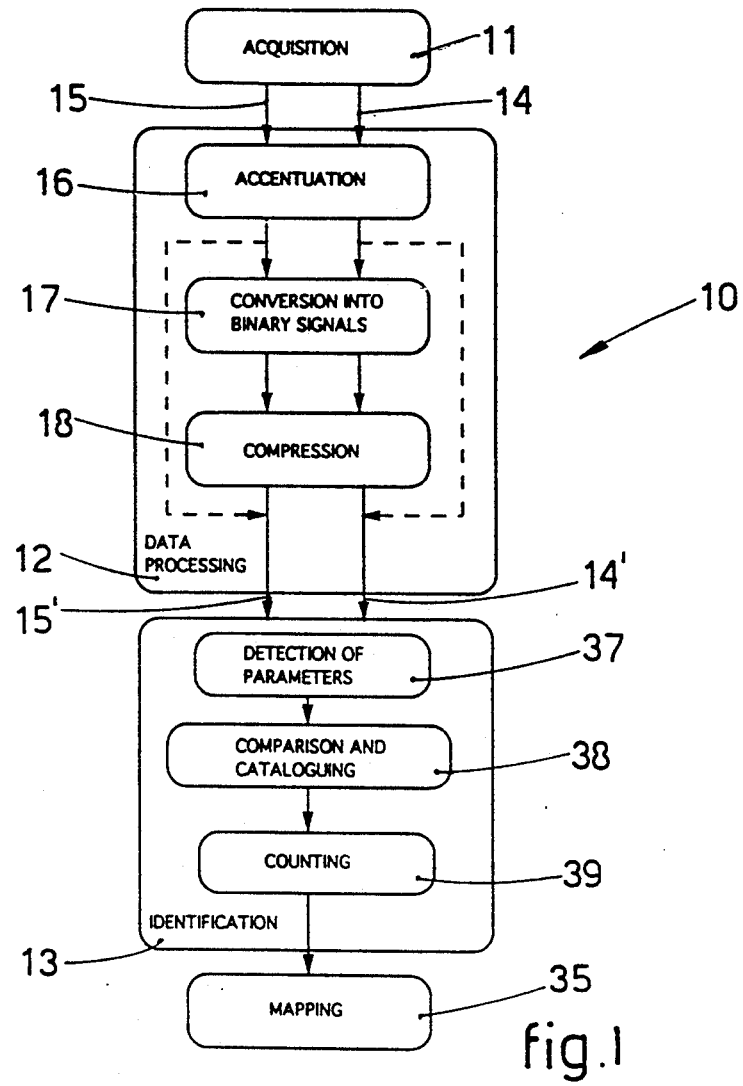
FIG. 1 shows a block diagram of the method according to the invention.

A method 10 to detect man-made fibers and/or defective fibers and/or other foreign materials in the process of silk waste comprises substantially the following steps, as shown in FIG. 1:

11—acquiring the image of the lap of silk fibers to be checked;

12—processing the images acquired in the previous acquiring step 11;

13—identifying the faults, and in particular, the man-made fibers contained in the segment of the lap of silk fibers under examination.

According to the invention two images are obtained of the same zones of the lap of silk fibers during the acquiring step 11, in particular an image obtained with a source of white light 14 and an image obtained with a source of polarized light 15.

According to a variant the source of white light 14 is suitably filtered and/or coloured.

In this example the data processing step 12 consists, in a known manner, of three procedures, namely an accentuation procedure 16, a procedure of conversion into binary signals 17 and a compression procedure 18.

According to a variant the procedure of conversion into binary signals 17 and/or the compression procedure 18 are eliminated.

In the method according to the invention the accentuation procedure 16 has been adapted to identify the faults in the lap of silk fibers and, in particular, to identify the contaminating man-made fibers.

In particular, the procedure 16 of accentuation of the image taken with white light 14 accentuates the fibers which are more opaque than the silk fibers; these more opaque fibers include the clusters of slightly intertwined silk fibers and the contaminating fibers.

The procedure 16 of accentuation of the image taken with polarized light 15 accentuates the fibers which cause rotation of the plane of polarization of the polarized light. This last step accentuates the polypropylene fibers comprised in the lap of silk fibers since the polypropylene fibers alone have the characteristic of rotating the plane of polarization of the polarized light.

The identification step 13 includes the combined analysis of data 14' and 15' obtained in the step 12 of processing the two images 14–15 obtained with the white light and polarized light respectively.

In the identification step 13 the contaminating fibers are classified which are detected by analysis of the data 14' obtained by analysis of the image taken with white light 14 on the basis of a plurality of classes, each of which defines an exact fault.

In particular, the identification step 13 includes a step of detection 37 of the characteristic parameters of the contaminating fibers identified.

In particular, values are obtained of some properties such as thickness, length, lack of continuity and opacity of the contaminating fiber.

Thereafter these characteristic parameters are compared 38 with analogous characteristic parameters determining an assembly of classes of faults so as to catalogue the contaminating fiber in a precise class of fault.

These classes of faults are characterized by well defined fields of the values of these characteristic parameters, so that the classes are separated and not superimposed; in this way the contaminating fiber can be listed in one single class of fault.

Where the properties of the contaminating fiber are not such as to enable the fault to be catalogued as belonging to one single class, then the contaminating fiber is listed in a special class called "unidentified fault".

Each class of fault is characterized by its own counter means, which is set to a higher value during the counting step 39 whenever a contaminating fiber is catalogued as forming part of that class of fault.

It is thus possible to know, in the case of each lap of silk fiber, the number of separate detected faults per type of fault and to catalogue the silk lap according to the number and type of faults encountered.

In particular, the combination of the data 14'–15' provides automatically, for instance, the value of the polypropylene fibres present within the lap of silk fibres being examined and thus enables the lap of silk fibers to be classified also according to the quantity of polypropylene fibers contained therein.

According to a variant a mapping step 35 is included after the identification step 13 and can be used in a machine or equipment to eliminate, even selectively, the faults or a part of the same.

Figure 2:
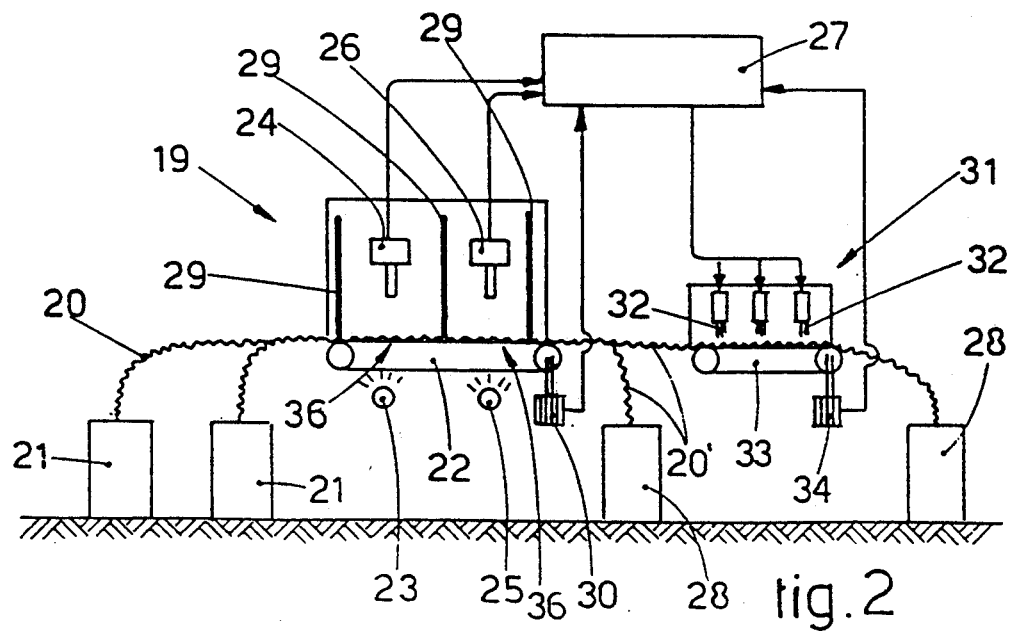
FIG. 2 is a diagram of an apparatus according to the invention.

FIG. 2 is a diagram of an apparatus 19 to detect man-made fibers in a lap 20 of silk fibers. In this example the lap of silk fibers 20, which has its fibers made substantially parallel and emerges from cans 21, is fed along a conveyor belt 22 at a speed between 3 and 10 meters per minute, advantageously 4 to 6 meters per minute.

The conveyor belt 22 is driven by an appropriate motor 30 which is connected to a data processing unit 27.

The lap 20 of silk fibers, when it passes over an appropriate transparent surface 36, is illuminated by transparency by a first luminous source of white light 23 and is scanned by a first telecamera 24; it is then illuminated by a second luminous source of polarized light 25 and scanned by a second telecamera 26.

In the apparatus 19 according to the invention the luminous sources 23-25 and respective telecameras 24-26 are positioned respectively on the same axis as, and on opposite sides of, the lap 20 of silk fibers being examined, that is to say, the lap 20 of silk fibers runs between the respective luminous source 23-25 and relative telecamera 24-26.

In this example the luminous sources 23-25 are positioned below the lap 20 of silk fibers, whereas the telecameras 24-26 are positioned above the lap 20 in positions coordinated with the respective luminous sources 23-25.

In the apparatus 19 according to the invention the axes of the luminous sources 23-25 and telecameras 24-26 may be horizontal or vertical or be inclined as desired.

The scanning by the telecameras 24-26 is coordinated with the forward movement of the conveyor belt 22 and therefore with the feed of the lap 20 of silk fibers, so that the zones scanned by the first telecamera 24 always coincide with the zones scanned by the second telecamera 26.

In the method 10 according to the invention the order in which the scannings are performed is unimportant inasmuch as the results are the same if the scanning with polarized light is carried out first and the scanning with white light is performed thereafter.

In fact, in the identification step 13 the data processing unit 27, receiving not only the images 14 and 15 but also the data of the speed of the conveyor belt 22, analyses at the same time the scannings of the same zone of the lap 20 of silk fibers.

The zones of illumination and scanning are screened by shields 29, which are advantageously black and non-reflecting, so as to avoid reflections or other difficulties.

The images 14-15 obtained by the first and second telecameras 24-26 respectively are transmitted to the data processing unit 27, in which they are processed so as to obtain as reliably as possible the identification of any man-made fibers and, in particular, any polypropylene fibers and/or defective fibers and/or other foreign substances in the lap 20 of silk fibers.

The data processing unit 27 can also list the detected contaminating fibers in an assembly of classes, each of which identifies a particular type of fault, by comparing the characteristic values of the contaminating fibers with the characteristic values defining those classes of faults.

The lap 20 of silk fibers, after this inspection, is collected in an appropriate can 28 or is passed beforehand through an assembly 31 which eliminates the faults and comprises operational means 32, which remove, even selectively, any faults encountered.

In this case the fault eliminating assembly 31 comprises a conveyor belt 33 driven by a motor 34 linked to the data processing unit 27 so as to ensure that the apparatus 19 detecting the faults is synchronized with the fault eliminating assembly 31 in order to remove such faults, even selectively.

We claim:

1. Method to detect at least one of man-made fibers, defective fibers and other foreign materials in the processing of silk waste and to classify and count the faults detected in a lap of substantially parallel silk fibers comprising the steps of:
   illuminating a substantially defined zone of the lap of silk fibers by transparency with white light while scanning the substantially defined zone of the lap of silk fibers by a telecamera associated with a data processing system; illuminating the substantially defined zone by transparency with polarized light while scanning the substantially defined zone of the lap of silk fibers with a telecamera associated with the data processing system; processing images taken by the telecamera(s); and comparing the images to predetermined characteristics of faults to determine at least one of the quantity, position, type and length of faults in the lap of silk fibers and of the man-made, foreign or defective fiber.

2. Method as in claim 1, whereby the white light and relative telecamera are associated with a quality control system.

3. Method as in claim 1, whereby the polarized light and the relative telecamera are associated with a quality control system.

4. Method as in claim 1, whereby the lap of silk fibers is produced from silk waste and is fed forwards substantially continuously, means being included to read a speed of feed of the lap of silk fibers and being associated with the data processing system.

5. Method as in claim 4, wherein said speed of feed of the lap of silk fibers is between 3 and 10 meters.

6. Method as in claim 4, wherein said speed of feed of the lap of silk fibers is between 4 and 6 meters per minute.

7. Method as in claim 1, whereby the data processing system is associated with an identification system.

8. Method as in claim 7, whereby the identification system includes the detection of parameters, their comparison and the cataloguing and the counting of faults.

9. Method as in claim 8, whereby the counting provides a counter means for each fault catalogued.

10. Method as in claim 7, whereby the identification system is associated with a mapping assembly.

11. Method as in claim 10, whereby an assembly to eliminate faults extends below the mapping assembly and is located downstream of the substantially defined zone.

12. Apparatus to detect man-made fibers in the processing of silk waste in the form of fibers and to classify and count faults detected in a lap of substantially parallel silk fibers, comprising:
   a transparent surface on which is laid the lap of silk fibers;
   a source of white light provided to illuminate the transparent surface;
   a source of polarized light provided to illuminate the transparent surface; the source of white light and the source of polarized light cooperating with at least one telecamera positioned on the opposite side of the transparent surface; and
   a data processing unit for identifying, classifying and counting faults in the lap of silk fibers.

13. Apparatus as in claim 12, in which one telecamera is included for each source of light shields being also included between telecameras to prevent disturbances.

14. Apparatus as in claim 12, in which a conveyor belt is included together with speed detection means associated with the data processing unit.

15. Apparatus as in claim 14, further comprising means for driving said conveyor belt at a speed between three and 10 meters per minute.

16. Apparatus as in claim 14, further comprising means for driving said conveyor belt at a speed between 4 and 6 meters per minute.

17. Apparatus as in claim 12, in which the data processing unit is associated with an identification unit and a mapping assembly.

18. Apparatus as in claim 12, in which an assembly for at least partial removal of faults is included and is associated with the data processing unit.

* * * * *